(12) United States Patent
Hiltner et al.

(10) Patent No.: US 10,779,796 B2
(45) Date of Patent: Sep. 22, 2020

(54) POSITION SENSING IN INTRAVASCULAR IMAGING

(71) Applicant: ACIST Medical Systems, Inc., Eden Prairie, MN (US)

(72) Inventors: Jason F. Hiltner, Minnetonka, MN (US); Robert F. Wilson, Roseville, MN (US); Sidney D. Nystrom, Shoreview, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 470 days.

(21) Appl. No.: 15/629,988

(22) Filed: Jun. 22, 2017

(65) Prior Publication Data

US 2017/0281133 A1 Oct. 5, 2017

Related U.S. Application Data

(63) Continuation of application No. 14/143,801, filed on Dec. 30, 2013, now Pat. No. 9,713,456.

(51) Int. Cl.
*A61B 8/12* (2006.01)
*A61B 8/00* (2006.01)
(Continued)

(52) U.S. Cl.
CPC .......... *A61B 8/4254* (2013.01); *A61B 5/0066* (2013.01); *A61B 5/0084* (2013.01);
(Continued)

(58) Field of Classification Search
CPC ....... A61B 8/4254; A61B 8/12; A61B 8/4263; A61B 34/30; A61B 5/0066; A61B 5/0084; A61B 5/743; A61B 5/066
See application file for complete search history.

(56) References Cited

U.S. PATENT DOCUMENTS

| 4,756,313 A | 7/1988 | Terwilliger |
| 5,244,461 A | 9/1993 | Derlien |

(Continued)

FOREIGN PATENT DOCUMENTS

| AU | 2013201648 B2 | 4/2014 |
| EP | 1929954 A1 | 6/2008 |

(Continued)

OTHER PUBLICATIONS

European Patent Application No. 09836694, Supplementary European Search Report dated May 19, 2015, 8 pages.

(Continued)

*Primary Examiner* — Joanne M Hoffman
(74) *Attorney, Agent, or Firm* — Fredrikson & Byron, P.A.

(57) ABSTRACT

An intravascular imaging system can include a catheter, a position sensor, and an intravascular imaging engine for receiving information from the catheter and the position sensor. The position sensor can include a reference element and a movable element, which can have a movable element position that is correlated to the position of an imaging transducer in the catheter. The relative position between the movable element and a reference element can be determined and can correspond to the relative movement of the transducer within a patient's vasculature. The imaging engine can receive position information from the position sensor and image information from the catheter and generate a display using the received information. Because relative movement of the transducer can be determined, spatial relationships between sets of imaging data can be determined, and image data from multiple transducer locations can be combined into one image.

22 Claims, 8 Drawing Sheets

(51) Int. Cl.
*A61B 5/00* (2006.01)
*A61B 5/06* (2006.01)
*A61B 34/30* (2016.01)
*A61B 8/08* (2006.01)
*A61B 5/02* (2006.01)
*A61B 90/00* (2016.01)

(52) U.S. Cl.
CPC .............. *A61B 5/066* (2013.01); *A61B 5/743* (2013.01); *A61B 8/12* (2013.01); *A61B 8/4263* (2013.01); *A61B 34/30* (2016.02); *A61B 5/02007* (2013.01); *A61B 8/0891* (2013.01); *A61B 8/445* (2013.01); *A61B 8/4483* (2013.01); *A61B 8/461* (2013.01); *A61B 8/5207* (2013.01); *A61B 2090/0811* (2016.02); *A61B 2090/3735* (2016.02); *A61B 2090/3782* (2016.02)

(56) References Cited

U.S. PATENT DOCUMENTS

| | | | |
|---|---|---|---|
| 5,327,885 A | 7/1994 | Griffith | |
| 5,361,768 A | 11/1994 | Webler et al. | |
| 5,827,313 A | 10/1998 | Ream et al. | |
| 5,908,395 A | 6/1999 | Stalker et al. | |
| 6,004,269 A | 12/1999 | Crowley et al. | |
| 6,004,271 A | 12/1999 | Moore et al. | |
| 6,035,229 A * | 3/2000 | Silverstein | A61B 1/00082 600/117 |
| 6,251,078 B1 | 6/2001 | Moore et al. | |
| 6,263,230 B1 | 7/2001 | Haynor | |
| 6,292,681 B1 | 9/2001 | Moore | |
| 6,319,227 B1 | 11/2001 | Mansouri-Ruiz | |
| 6,321,106 B1 | 11/2001 | Lemelson | |
| 6,398,755 B1 | 6/2002 | Belef et al. | |
| 6,511,432 B2 | 1/2003 | Moore et al. | |
| 6,592,520 B1 * | 7/2003 | Peszynski | A61B 8/12 600/437 |
| 6,974,465 B2 | 12/2005 | Belef et al. | |
| 8,157,741 B2 | 4/2012 | Hirota | |
| 8,298,156 B2 * | 10/2012 | Manstrom | A61M 5/007 600/561 |
| 9,138,148 B2 * | 9/2015 | Sliwa | A61B 5/0053 |
| 9,492,638 B2 * | 11/2016 | McKinnis | A61B 8/12 |
| 2001/0021841 A1 | 9/2001 | Webler et al. | |
| 2001/0045935 A1 | 11/2001 | Chang et al. | |
| 2001/0047165 A1 | 11/2001 | Makower et al. | |
| 2002/0047367 A1 | 4/2002 | Kim et al. | |
| 2002/0050169 A1 | 5/2002 | Ritter et al. | |
| 2002/0093880 A1 | 7/2002 | Nakamura | |
| 2002/0107447 A1 | 8/2002 | Suorsa et al. | |
| 2002/0183723 A1 | 12/2002 | Belef et al. | |
| 2003/0013958 A1 * | 1/2003 | Govari | A61B 5/0422 600/437 |
| 2003/0135995 A1 | 7/2003 | Glasson | |
| 2003/0171678 A1 * | 9/2003 | Batten | A61B 8/0833 600/443 |
| 2003/0187369 A1 | 10/2003 | Lewis et al. | |
| 2004/0078036 A1 | 4/2004 | Keidar | |
| 2004/0133105 A1 * | 7/2004 | Ostrovsky | A61B 5/06 600/437 |
| 2004/0147920 A1 | 7/2004 | Keidar | |
| 2004/0215130 A1 | 10/2004 | Rioux et al. | |
| 2005/0054929 A1 | 3/2005 | Angelsen et al. | |
| 2006/0106375 A1 * | 5/2006 | Werneth | A61B 18/1492 606/32 |
| 2006/0122514 A1 * | 6/2006 | Byrd | A61B 5/06 600/466 |
| 2006/0241445 A1 * | 10/2006 | Altmann | A61B 8/12 600/443 |
| 2006/0241469 A1 | 10/2006 | Rold et al. | |
| 2006/0241484 A1 | 10/2006 | Horiike et al. | |
| 2006/0287599 A1 | 12/2006 | Cimino | |
| 2007/0066890 A1 * | 3/2007 | Maschke | A61B 5/0066 600/424 |
| 2007/0093752 A1 | 4/2007 | Zhao et al. | |
| 2007/0106147 A1 * | 5/2007 | Altmann | A61B 8/12 600/407 |
| 2007/0135803 A1 | 6/2007 | Belson | |
| 2007/0167752 A1 | 7/2007 | Proulx et al. | |
| 2007/0167821 A1 | 7/2007 | Lee et al. | |
| 2008/0146941 A1 * | 6/2008 | Dala-Krishna | A61B 8/12 600/466 |
| 2008/0195041 A1 | 8/2008 | Goldfarb et al. | |
| 2008/0200801 A1 * | 8/2008 | Wildes | A61B 8/12 600/424 |
| 2008/0255449 A1 | 10/2008 | Warnking et al. | |
| 2008/0255475 A1 | 10/2008 | Kondrosky | |
| 2009/0054776 A1 | 2/2009 | Sasaki | |
| 2009/0069693 A1 | 3/2009 | Burcher et al. | |
| 2009/0124998 A1 | 5/2009 | Rioux et al. | |
| 2009/0137952 A1 * | 5/2009 | Ramamurthy | A61B 5/06 604/95.01 |
| 2009/0156941 A1 * | 6/2009 | Moore | A61B 5/02007 600/467 |
| 2009/0234220 A1 * | 9/2009 | Maschke | A61B 5/411 600/411 |
| 2009/0234302 A1 | 9/2009 | Hoendervoogt et al. | |
| 2009/0234445 A1 * | 9/2009 | Maschke | A61B 5/0066 623/2.11 |
| 2010/0016710 A1 | 1/2010 | Kumar et al. | |
| 2010/0057019 A1 | 3/2010 | Zelenka | |
| 2010/0152590 A1 | 6/2010 | Moore et al. | |
| 2010/0179434 A1 | 7/2010 | Thornton | |
| 2010/0249603 A1 | 9/2010 | Hastings et al. | |
| 2011/0021924 A1 | 1/2011 | Sethuraman et al. | |
| 2011/0184406 A1 | 7/2011 | Selkee | |
| 2011/0230906 A1 | 9/2011 | Modesitt | |
| 2012/0071752 A1 | 3/2012 | Sewell et al. | |
| 2012/0150035 A1 | 6/2012 | Seip et al. | |
| 2013/0137963 A1 | 5/2013 | Olson | |
| 2013/0172713 A1 * | 7/2013 | Kirschenman | A61B 5/042 600/373 |
| 2013/0274657 A1 | 10/2013 | Zirps et al. | |
| 2014/0039294 A1 * | 2/2014 | Jiang | A61B 8/12 600/409 |
| 2014/0163361 A1 * | 6/2014 | Stigall | A61B 5/0073 600/427 |
| 2014/0180127 A1 * | 6/2014 | Meyer | A61B 8/0891 600/467 |
| 2014/0343433 A1 | 11/2014 | Elbert | |
| 2015/0038824 A1 * | 2/2015 | Lupotti | A61B 8/12 600/407 |
| 2015/0065956 A1 | 3/2015 | Huang | |
| 2016/0081657 A1 * | 3/2016 | Rice | A61B 8/445 600/301 |
| 2016/0220314 A1 | 8/2016 | Huelman | |

FOREIGN PATENT DOCUMENTS

| | | |
|---|---|---|
| EP | 1952768 A2 | 8/2008 |
| EP | 2358278 A2 | 8/2011 |
| EP | 2749240 A2 | 7/2014 |
| JP | 63122923 A | 5/1988 |
| JP | 63281632 A | 11/1988 |
| JP | 63302836 A | 12/1988 |
| JP | 04017843 A | 1/1992 |
| JP | 05244694 A | 9/1993 |
| JP | 07008497 A | 1/1995 |
| JP | 07095980 A | 4/1995 |
| JP | 07136171 A | 5/1995 |
| JP | 07184902 A | 7/1995 |
| JP | 07508204 A | 9/1995 |
| JP | 08112286 A | 5/1996 |
| JP | 2000157546 A | 6/2000 |
| JP | 2002301070 A | 10/2002 |
| JP | 2003265483 A | 9/2003 |
| JP | 2004209277 A | 7/2004 |
| JP | 2005507273 A | 3/2005 |
| JP | 2005536289 A | 12/2005 |
| JP | 2006102240 A | 4/2006 |

(56) References Cited

FOREIGN PATENT DOCUMENTS

| | | |
|---|---|---|
| JP | 2007105450 A | 4/2007 |
| JP | 2007152094 A | 6/2007 |
| JP | 2007268132 A | 10/2007 |
| JP | 2008053887 A | 3/2008 |
| JP | 2008155022 A | 7/2008 |
| JP | 2008178676 A | 8/2008 |
| JP | 2008277834 A | 11/2008 |
| JP | 2008539887 A | 11/2008 |
| JP | 2012510885 A | 5/2012 |
| WO | 9203095 A1 | 3/1992 |
| WO | 2003011139 A1 | 2/2003 |
| WO | 2007044792 A1 | 4/2007 |
| WO | 2008042423 A2 | 4/2008 |
| WO | 2008086613 A1 | 7/2008 |
| WO | 2010077632 A2 | 7/2010 |
| WO | 2010107916 A1 | 9/2010 |
| WO | 2011058493 A1 | 5/2011 |
| WO | 2015102573 A1 | 7/2015 |

OTHER PUBLICATIONS

International Patent Application No. PCT/US2009/067094, International Search Report & Written Opinion dated Jul. 20, 2010, 10 pages.
Japanese Patent Application No. 2015-151658, Notice of Reasons for Refusal dated Jul. 28, 2016, 6 pages (including 3 pages English Machine Translation).
Japanese Patent Application No. 2015-151658, Search Report dated Jul. 25, 2016, 30 pages (including 13 pages English Machine Translation).
Casaclang-Verzosa, G. et al., "Structural and functional remodeling of the left atrium," Journal of American College of Cardiology, vol. 51, No. 1, Jan. 2008, 11 pgs.

* cited by examiner

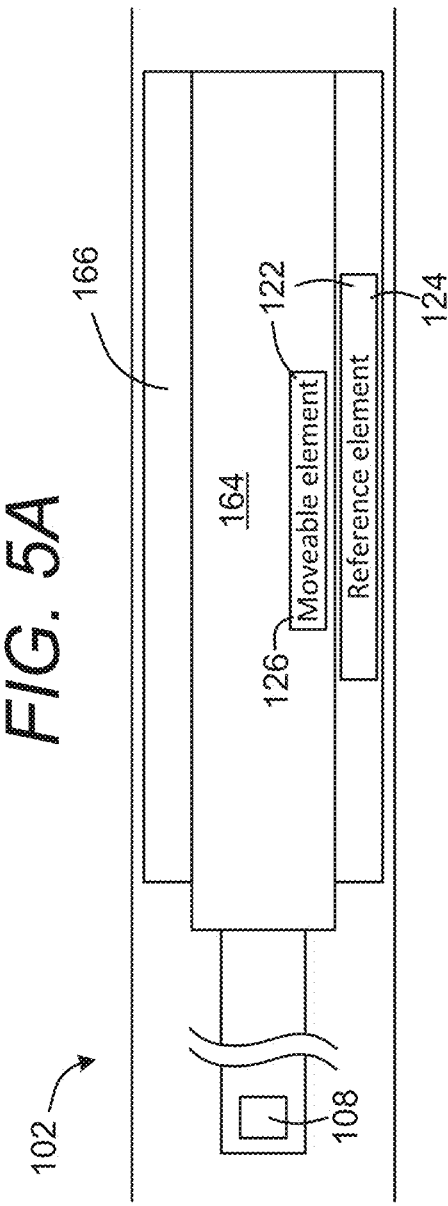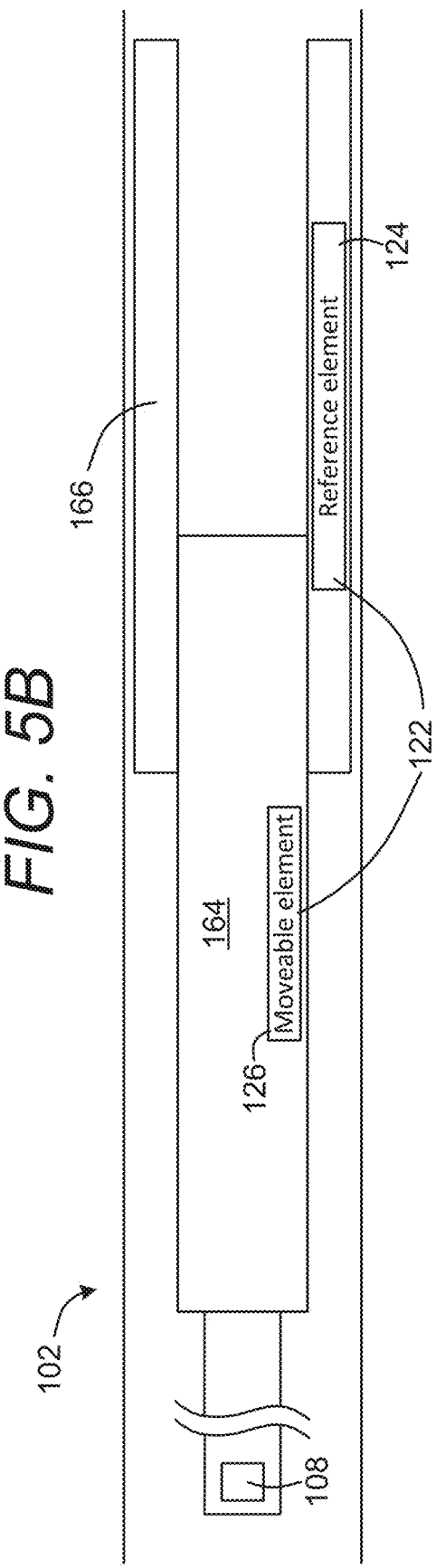

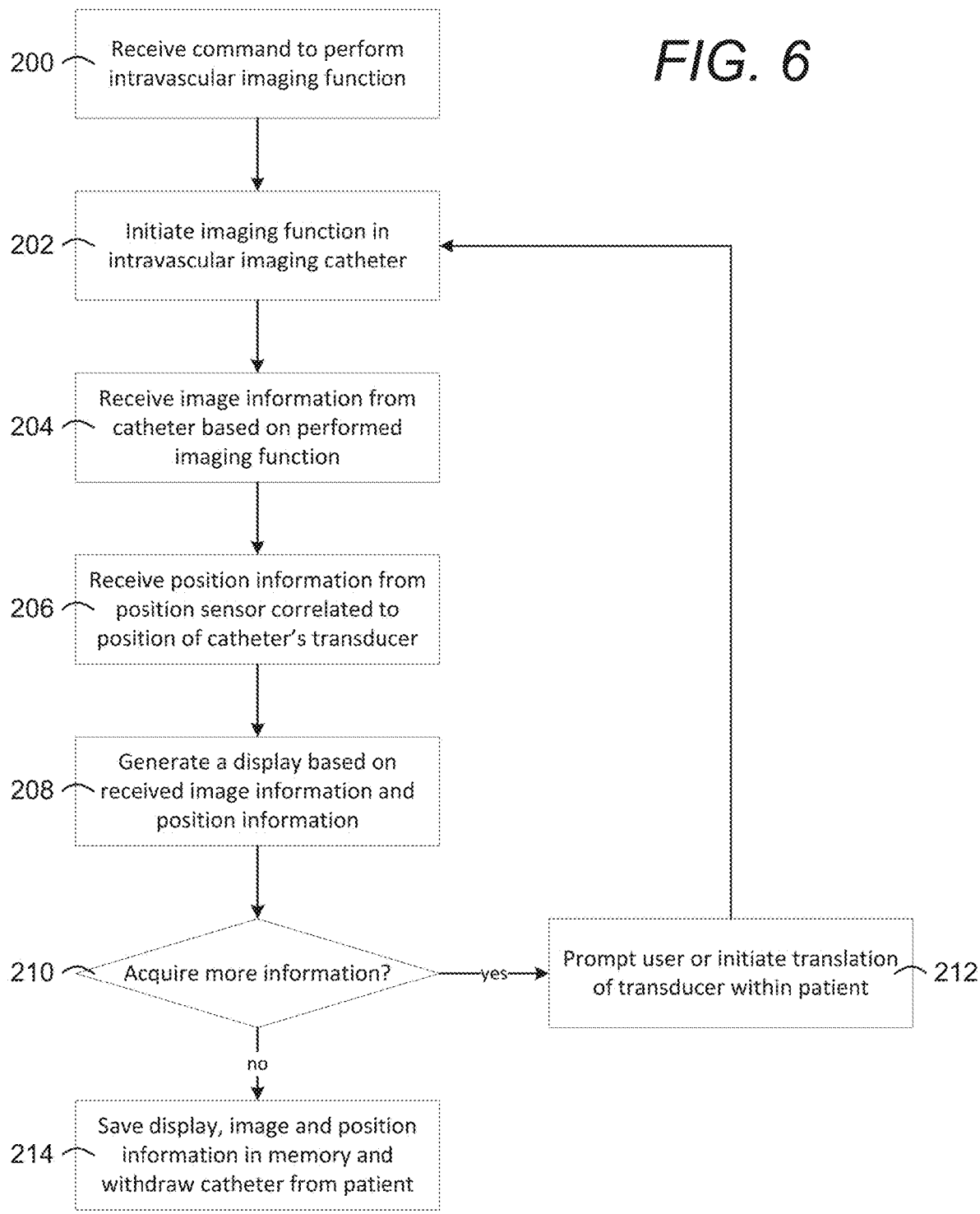

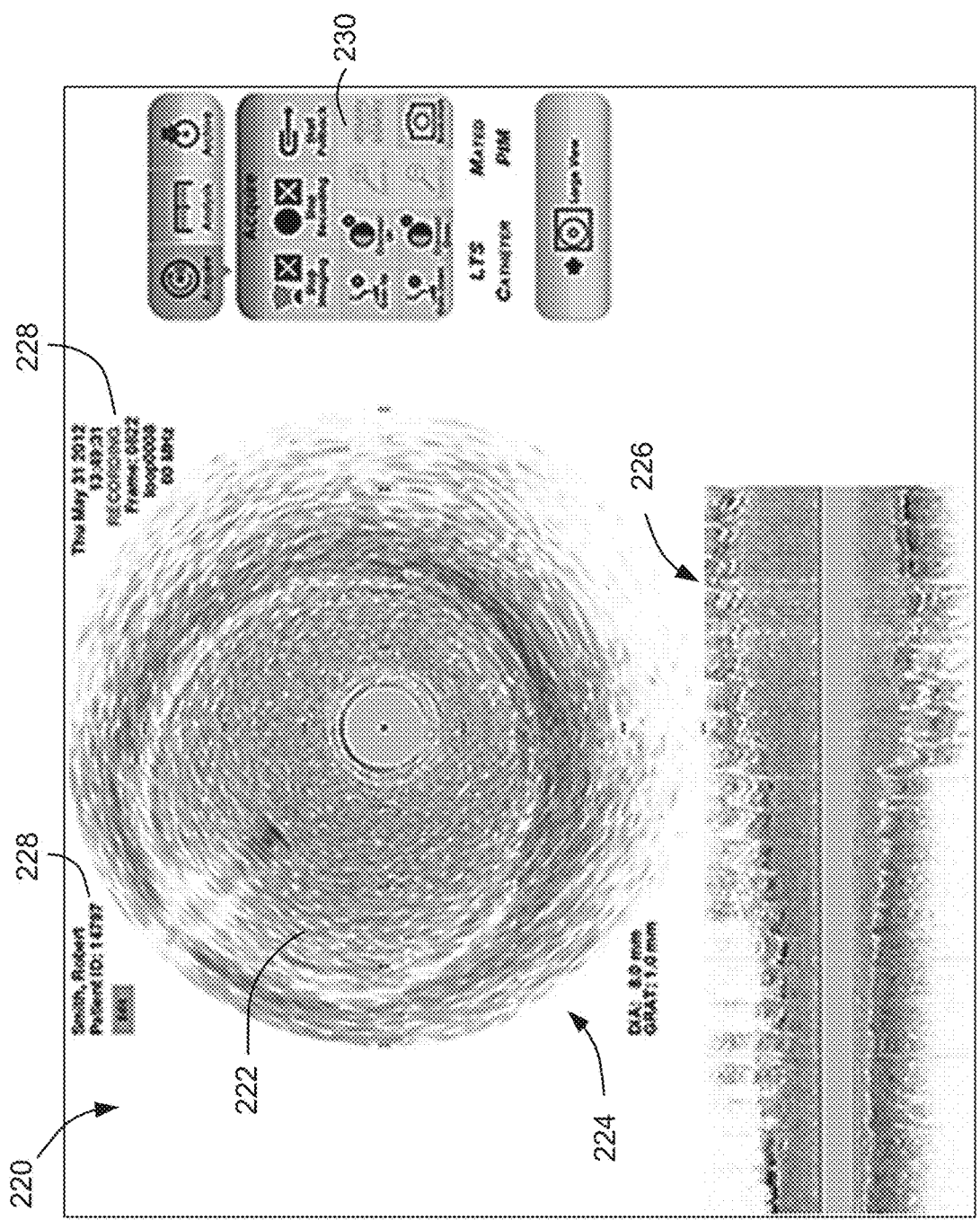

POSITION SENSING IN INTRAVASCULAR IMAGING

CROSS-REFERENCES

This application is a continuation of U.S. patent application Ser. No. 14/143,801, filed Dec. 30, 2013.

TECHNICAL FIELD

This disclosure relates to an intravascular imaging system and a method of operating the same.

BACKGROUND

Intravascular imaging is often used to identify diagnostically significant characteristics of a vessel. For example, an intravascular imaging system may be used by a healthcare professional to help identify and locate blockages or lesions in a vessel. Common intravascular imaging systems include intravascular ultrasound (IVUS) systems as well as optical coherence tomography (OCT) systems.

Intravascular imaging involves one or more transducers emitting and/or receiving energy based on received electrical signals and sending return electrical signals based on signals reflected by various intravascular structures. Intravascular imaging is often used to generate images. In some instances, a console with a high-resolution display is able to display intravascular images in real-time. In this way, intravascular imaging can be used to provide in-vivo visualization of the vascular structures and lumens, including the coronary artery lumen, coronary artery wall morphology, and devices, such as stents, at or near the surface of the coronary artery wall. Intravascular imaging may be used to visualize diseased vessels, including coronary artery disease. In some instances, the transducer(s) can be carried near a distal end of an intravascular imaging catheter. Some intravascular imaging systems involve rotating the intravascular imaging catheter (e.g., mechanically, phased-array, etc.) for 360-degree visualization.

Many intravascular imaging systems are configured to perform translation operations, in which imaging components of the catheter are translated through a patient's blood vessel while acquiring images. The result is a 360-degree image with a longitudinal component. When performing a translation operation, it can be important to accurately determine at least the relative amount of translation of the catheter's imaging components in order to accurately construct the 360-degree image.

In existing systems, the amount of translation is often estimated by attempting to translate the catheter at a certain velocity for a certain amount of time. If the catheter's imaging components are translated at a certain velocity for a certain time, the translated distance can be calculated. However, if the actual translation velocity is not the same as the commanded velocity, or cannot be reliably measured or produced, inaccuracies in determining the amount of translation can occur. Inaccurate translation determinations can lead to errors in constructing the 360-degree image with longitudinal component.

SUMMARY

Embodiments of intravascular imaging systems discussed in this disclosure can detect the real-time position of a catheter's transducer(s), which can lead to more accurate intravascular images that have a longitudinal component.

Many intravascular imaging catheter embodiments include one or more transducers in the distal end. A position sensor can include a reference element and a movable element, and the position of the movable element can be correlated to the position of the transducer(s). With the positions of the movable element and the transducer(s) correlated to one another, the position of the transducer(s) relative to that of the reference element can be determined from the position of the movable element relative to that of the reference element. In many embodiments, an intravascular imaging engine can generate displays based on such position information and on image information received from the transducer(s). The intravascular imaging engine can receive image information associated with several movable element positions and can generate an intravascular image (e.g., in real-time) that has a longitudinal component. The unique movable element positions associated with each set of position and image information can be correlated to a unique transducer location within a patient's vasculature.

In various embodiments, position sensors can be located in different places in the intravascular imaging system. For example, the reference element and the movable element can be located on components of a translation mechanism that translates the catheter within the patient's vasculature (e.g., automatically or manually). In another example, the reference component can be located in a reference medical component, such as a surgical mat. In another example, the reference element and the movable element can be located on components of the catheter. Many combinations and configurations are possible and contemplated according to the subject matter provided herein.

BRIEF DESCRIPTION OF DRAWINGS

FIGS. 5A and 5B are side views of first and second telescoping portions of an illustrative intravascular imaging catheter.

FIG. 6 is a step-flow diagram of an illustrative method for generating one or more displays.

FIG. 7 shows an illustrative longitudinal image.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
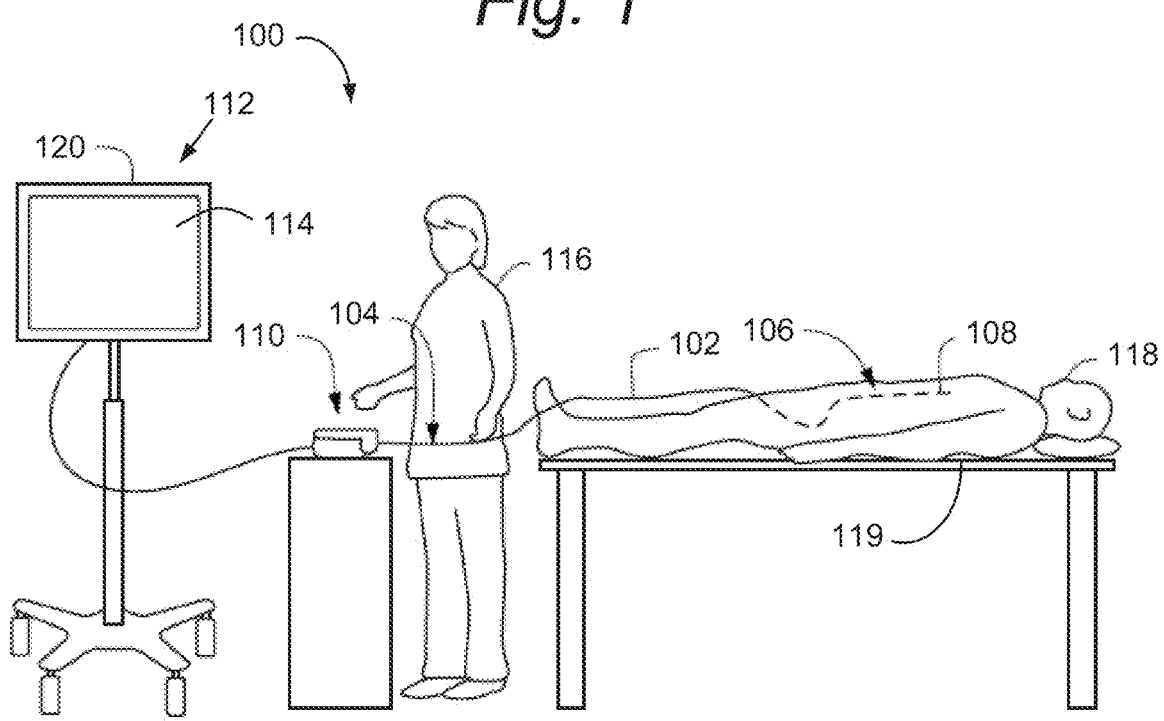
FIG. 1 is an illustrative intravascular imaging system.

FIG. 1 is an illustrative example of a system 100 that may be configured to perform intravascular imaging. System 100 may include a catheter 102, a translation mechanism 110, and an imaging engine 112. The catheter 102 may include a proximal end 104 and a distal end 106 configured to be inserted into a vessel of a patient 118. As shown, patient 118 is positioned on an operating table, which may comprise a surgical mat 119. In one example, catheter 102 may be inserted into the patient 118 via the femoral artery and guided to an area of interest within the patient 118. The broken lines in FIG. 1 represent portions of catheter 102 within the patient 118.

In some examples, catheter 102 may include a transducer 108 within distal end 106 configured to emit and receive wave-based energy and generate imaging data—e.g., to image the area of interest within the patient 118. For example, where system 100 is an IVUS system, transducer 108 may comprise an ultrasound transducer configured to emit and receive ultrasound energy and generate ultrasound data. In another example, system 100 may be an OCT system, and transducer 108 may comprise an OCT transducer configured to emit and receive light and generate OCT data. The catheter 102 can be configured to generate image information and transmit that image information for imaging.

The translation mechanism 110 of the intravascular imaging system 100 can be engaged with the catheter 102 and configured to translate the catheter 102 a controlled distance within the patient 118 during a pullback or other translation operation. In some embodiments, the translation mechanism 110 can act as an interface with the catheter 102. The translation mechanism 110 can translate all or part of the catheter 102 through the vasculature of the patient 118. For example, in an embodiment in which the catheter comprises a drive cable attached to the transducer 108 housed within a sheath, the translation mechanism 110 can act to translate the drive cable and transducer 108 through the sheath while keeping the sheath fixed.

The imaging engine 112 may be in communication with the transducer 108 and the translation mechanism 110. According to some examples, the imaging engine 112 may comprise at least one programmable processor. In some examples, the imaging engine 112 may comprise a computing machine including one or more processors configured to receive commands from a system user 116 and/or display data acquired from catheter 102 via a user interface 120. The computing machine may include computer peripherals (e.g., keyboard, mouse, electronic display) to receive inputs from the system user 116 and output system information and/or signals received from catheter 102 (e.g., rendered images). The user interface 120 may include a traditional PC or PC interface with software configured to communicate with the other components of the intravascular imaging system 100. In some embodiments, the user interface 120 may include a display 114 configured to display system information and/or imaging signals from the catheter 102 (e.g., intravascular images). In some embodiments, the user interface 120 includes a touchscreen display, which can act to both receive commands from a system user 116 and display intravascular imaging data from the catheter 102. In some examples, imaging engine 112 may include memory modules for storing instructions, or software, executable by the one or more processors.

Figure 2:
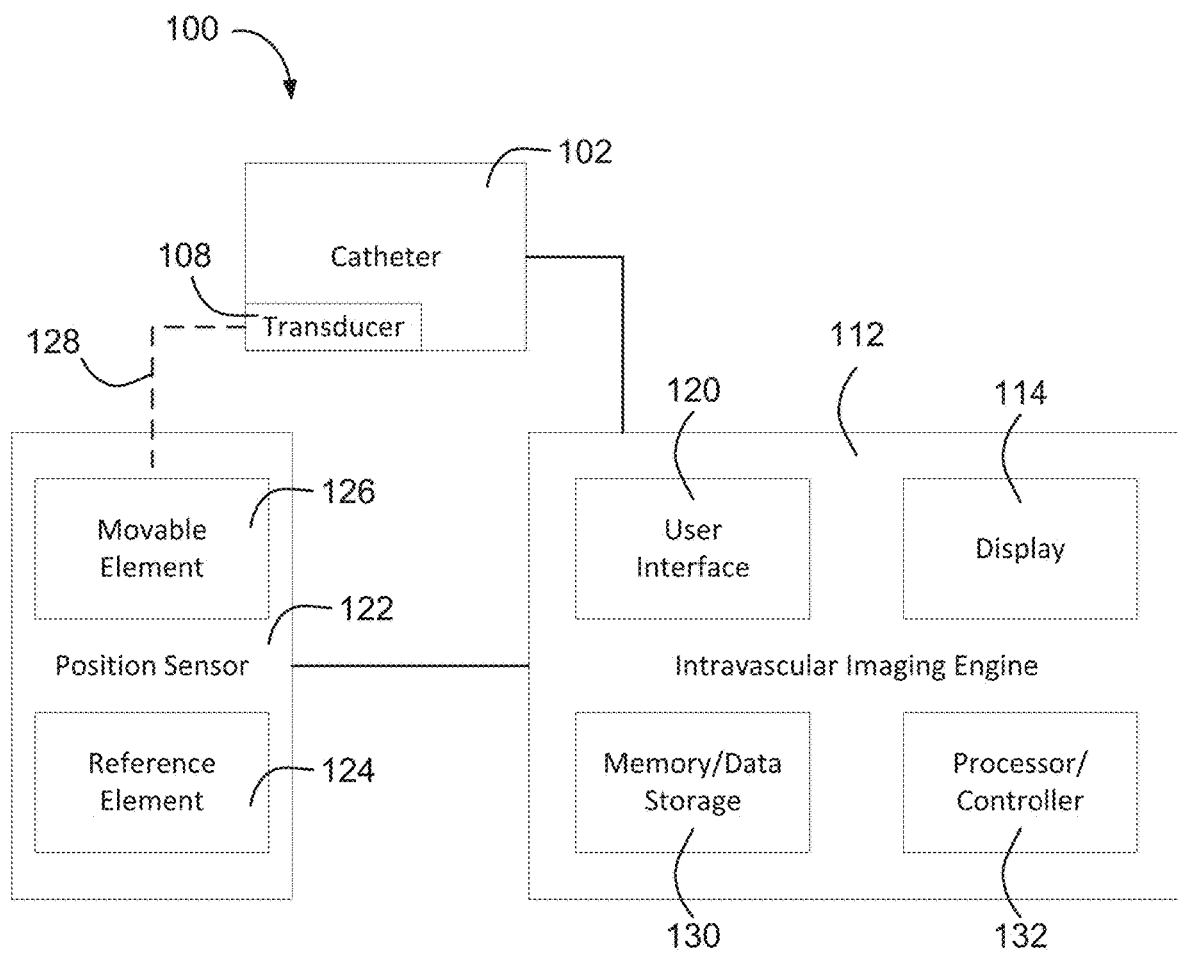
FIG. 2 is a system-level block diagram of an illustrative intravascular imaging system.

FIG. 2 is a system-level block diagram of an embodiment of an intravascular imaging system 100 that includes a position sensor 122. In particular, the illustrative system 100 of FIG. 2 comprises a catheter 102, a position sensor 122 and an intravascular imaging engine 112. The catheter 102 can include a transducer 108 and can be in communication with the intravascular imaging engine 112. In some embodiments, the intravascular imaging engine 112 is in direct communication with the transducer 108. In the embodiment of FIG. 2, the intravascular imaging engine 112 comprises a display 114, a user interface 120, memory/data storage 130 and a processor/controller 132. These components may be integrated into, for example, a touch screen display and/or a computer.

In some embodiments, the catheter 102 or the transducer 108 within the catheter 102 can be translated within a patient's vasculature while performing an imaging function. In such cases, the intravascular imaging engine 112 can receive image information from the transducer 108 at a plurality of transducer positions. In some embodiments, intravascular imaging engine 112 can receive the image information from a plurality of transducer positions and construct an aggregate longitudinal image which comprises image information from at least a subset of the plurality of transducer positions. To construct such an aggregate image, it can be useful for the intravascular imaging engine 112 to detect at least a relative relationship between the positions from which the image information was received. Accordingly, some embodiments of the intravascular imaging system 100 include a position sensor 122.

The position sensor 122 shown in FIG. 2 may include a movable element 126 and a reference element 124. The position sensor 122 can comprise, for example, a potentiometer, an encoder, a linear variable differential transformer, or other suitable position sensor. Such a position sensor 122 can be integrated into the intravascular imaging system 100 and placed in communication with the intravascular imaging engine 112. The movable element 126 of the position sensor 122 can have a movable element position that is correlated to the position of the transducer 108. The correlation between the transducer position and the position of the movable element 126 is represented by broken line 128 in FIG. 2. The reference element 124 of the position sensor 122 can be substantially fixed relative to motion of transducer 108 during intravascular imaging operation. In such embodiments, because of the correlation between the transducer position and the movable element position, the position sensor 122 can be configured to determine the relative motion of the transducer 108 with respect to the reference element 124 of the position sensor 122 can be determined. In some embodiments, the position sensor 122 can determine the relative motion of the transducer 108 with respect to the reference element 124, which the position sensor 122 can communicate to other components of the intravascular imaging engine 112.

As shown in FIG. 2, the position sensor 122 can be in communication with the intravascular imaging engine 112. In some embodiments, the intravascular imaging engine 112 can be configured to receive position information from the position sensor 122. Position information can comprise information regarding the position of the movable element 126 of the position sensor 122 relative to the reference element 124. The position information can include information received from an encoder, resistance information or other electrical data from a potentiometer, or any other signals or information from various kinds of position sensors. In embodiments in which the position sensor 122 determines the relative motion of the transducer 108 with respect to the reference element 124, the position sensor 122 can provide that position information to the intravascular imaging engine 112. In some embodiments, the position sensor 122 can provide information regarding the movable element 126 and the reference element 124 to the intravascular imaging engine 112, and the intravascular imaging engine 112 can determine the relative motion of the transducer 108 with respect to the reference element 124. As discussed, the position of the movable element 126 can be correlated to the position of the transducer 108 of the catheter 102. In some embodiments, the position sensor 122 can compare the location of the movable element 126 with that of the reference element 124, account for how the location of the movable element 126 correlates to that of the transducer 108, and determine the location of the transducer 108 relative to that of the reference element 124. In such embodiments, the position sensor 122 can provide the location of the transducer 108 to the intravascular imaging engine 112. In some embodiments, the position sensor 122 can simply send information concerning the location of the movable element 126 relative to that of the reference element 124 to the intravascular imaging engine 112. In some such embodiments, the intravascular imaging engine 112 can compare the location of the movable element 126 with that of the reference element 124, account for how the location of the movable element 126 correlates to that of the transducer 108, and determine the location of the transducer 108 relative to that of the reference element 124.

In some embodiments, the intravascular imaging engine 112 can be configured to receive both image information from the intravascular imaging catheter 102 and position information from the position sensor 122. The intravascular imaging engine 112 can associate particular image information with a relative position of the transducer 108. The intravascular imaging engine 112 can be configured to generate a display based on the image information and the position information.

The intravascular imaging engine 112 can receive and process image information and position information corresponding to multiple longitudinal positions within the blood vessel being imaged. In some configurations, the intravascular imaging engine 112 can receive a first set of image information and a first set of position information, each corresponding to a first movable element position. The intravascular imaging engine can additionally receive a second set of image information and a second set of position information, each corresponding to a second movable element position. In general, the image information and position information can comprise information corresponding to any number of movable element positions. In some preferred embodiments, the intravascular imaging engine 112 can process image information and position information in real time for several locations during a transducer translation to provide real-time imaging of the blood vessel being imaged.

As discussed elsewhere herein, in some embodiments the movable element position is correlated to the position of the transducer 108. Thus, first and second sets of image and position information corresponding to first and second movable element positions can also correspond to first and second transducer positions. The transducer 108 can be translated within the patient's vasculature to various positions, while the movable element 126 can move relative to the reference element 124 correspondingly. The transducer 108 can be translated through the patient's vasculature in a number of ways. In some embodiments, the catheter 102 translates through the patient's vasculature. The transducer 108 can translate within the catheter 102, within a sheath, for example. In some embodiments, the intravascular imaging system can include a translation mechanism configured to translate the catheter 102 and/or the transducer 108 within the catheter 102.

Figure 3:
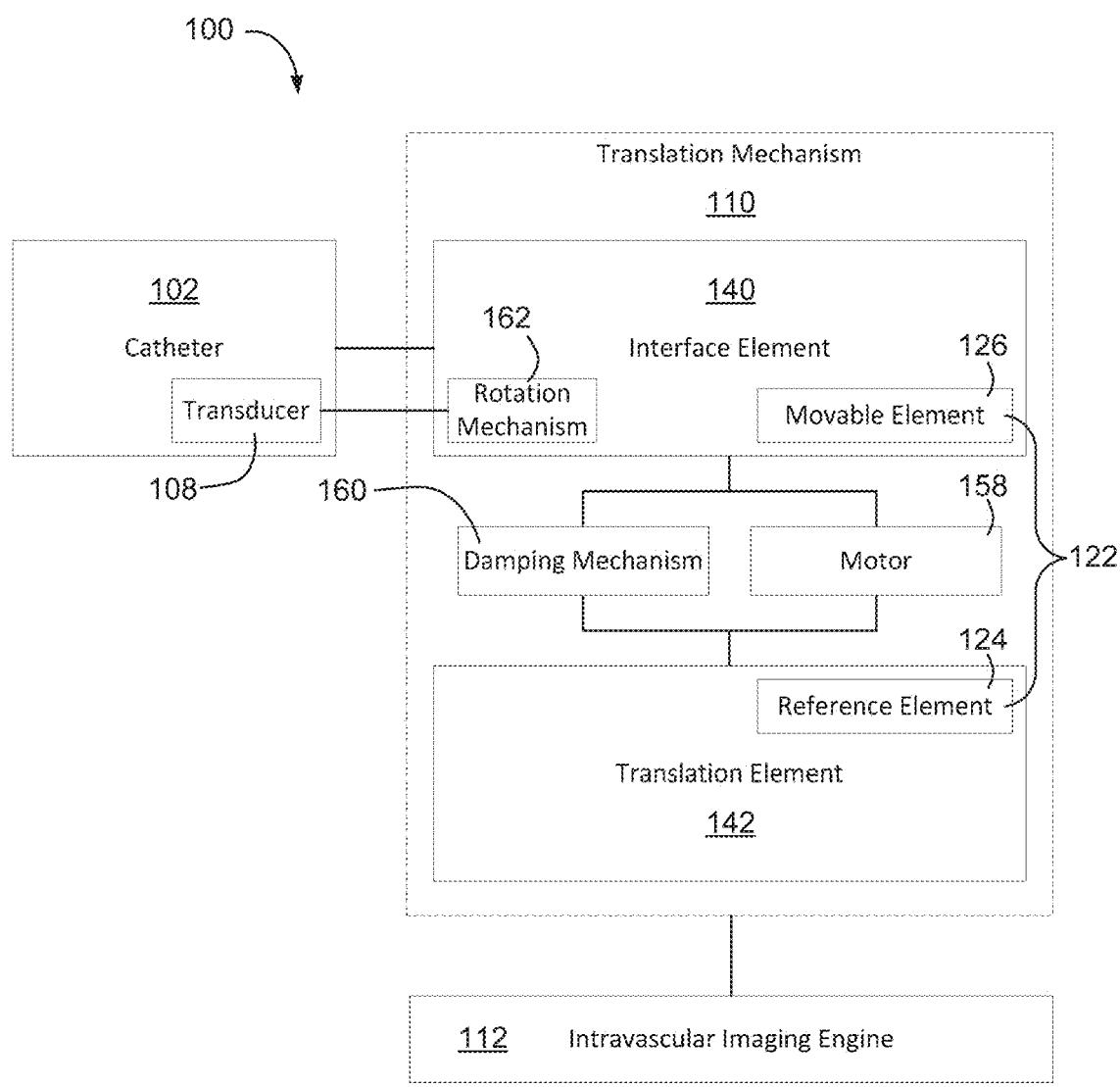
FIG. 3 is a system-level block diagram of an illustrative translation mechanism of some intravascular imaging systems.

Some translation mechanisms can include an interface element configured to engage at least a portion of the catheter 102 and a translation element configured to engage and translate the interface element. FIG. 3 is a system-level block diagram showing an illustrative translation mechanism 110 in an embodiment of an intravascular imaging system 100. The system 100 shown in FIG. 3 comprises a catheter 102 having a transducer 108. The system 100 can further include an intravascular imaging engine 112 configured to receive image information from the catheter 102 and generate a display. In some embodiments, the system 100 includes a position sensor having a reference element 124 and a movable element 126, the position sensor being generally configured as described elsewhere in this disclosure. The position sensor can provide position data to the intravascular imaging engine 112, which can be used by the engine 112 to generate the display.

In some embodiments, the system 100 can include a translation mechanism 110. The translation mechanism 110 can include a translation element 142 and an interface element 140. In some embodiments, the translation element 142 is configured to translate the interface element 140. Translation between the interface element 140 and the translation element can be achieved by a motor 158 incorporated into the translation mechanism 110. In some embodiments, translation between the interface element 140 and the translation element 142 can be performed manually by a user. The translation mechanism 110 can include a damping mechanism 160 to smooth translation.

The interface element 140 can provide a mechanical and/or electrical interface with the catheter 102. In some embodiments, the interface element 140 can comprise a rotation mechanism 162 configured to rotate the transducer 108. Rotation of the transducer 108 can be done in order to perform an imaging function. The interface element 140 can be in communication with the intravascular imaging engine 112. The intravascular imaging engine 112 can provide signals to the interface element 140 to cause it to rotate the transducer 108 via the rotation mechanism 162. In some embodiments, the interface element 140 provides the communication interface between the intravascular imaging engine 112 and the catheter 102 and/or transducer 108. Signals from the intravascular imaging engine 112 can be sent to the transducer 108 via an electrical interface between the catheter 102 and the interface element 140.

As described elsewhere in this disclosure, the relative movement of movable element 126 and the reference element 142 of the position sensor can be measured. In some embodiments, the position sensor 122 can be integrated into the translation mechanism 110. For example, the reference element 124 of the position sensor 122 can be secured to the translation element 142 of the translation mechanism 110, while the movable element 126 of the position sensor 122 can be secured to the interface element 140 of the translation mechanism 110, or vice versa.

Accordingly, in some embodiments, the position sensor 122 can provide information regarding the relative position between the interface element 140 and the translation element 142 of the translation mechanism 110. In some such embodiments, if the translation element 142 of the translation mechanism 110 is fixed relative to the patient and the interface element 140 is secured to the transducer 108, the position sensor 122 can provide information regarding the relative position of the transducer 108 within the patient. The intravascular imaging engine 112 can receive data from the translation mechanism 110. Such data can include image information generated by the transducer 108 sent to the intravascular imaging engine 112 via the interface element 140, and/or position information sent to the intravascular imaging engine 12 via the position sensor 122 in the translation mechanism 110.

The translation mechanism 110 can comprise a motor 158 to effect translation of the interface element 140 relative to the translation element 142. The motor 158 can be a servo-motor, a stepper motor, a linear induction motor, or other suitable motors. In some embodiments, the intravascular imaging engine 112 can be in communication with the motor 158. Communication can be established directly between the motor 158 and the engine 112. In some embodiments, the communication can be established via the translation mechanism 110. The intravascular imaging engine 112 can receive commands via a user interface to effect translation of the interface element 140 via the motor 158.

In some embodiments, translation by the motor can be automated by commands stored in memory 130 in communication with the intravascular imaging engine 112. That is, the translation mechanism 110 can be motorized for automatic translation. Automatic translation by the motor can be initiated by any number events, including but not limited to a prompt by a user, a pre-programmed operation sequence, and so on. During automatic translation, the motor can translate the interface element 140 relative to the translation element 142 by a predetermined distance. As described elsewhere herein, the relative position between the interface element 140 and the translation element 142 can be determined from the position sensor 122. Thus, in some embodiments, the intravascular imaging engine 112 can be in communication with the position sensor 122 and the translation mechanism 110 in order to actuate predetermined translation of the transducer 108. In some embodiments, the motor 158 can be secured directly to the catheter 102 or the transducer 108 in order to effect movement thereof without a discrete translation element 142 and/or interface element 140 of the translation mechanism 110.

The user can manually translate, for example, portions of the catheter 102 and/or transducer 108, or a portion of the translation mechanism 110, such as the interface element 140. Some operators prefer manual translation to automatic translation. In some instances, operators appreciate having the flexibility to manually move the transducer 108 to a specific position in order to review a particular area of interest in greater detail. Measuring, rather than predicting, the location of the transducer 108 can be important in many instances involving manual translation of the transducer.

In some embodiments, the translation mechanism 110 can include a damping mechanism configured to prevent abrupt motion of the transducer 108. Damping mechanism can smooth the translation of the transducer 108 by a spring-based mechanism, a hydraulic mechanism, or other suitable damping mechanism. Preventing abrupt or jerky motion of the transducer 108 and/or catheter 102 can improve the quality of an image produced by the system and prevent undesirably abrupt motion of components within a patient's body.

Figure 4A:
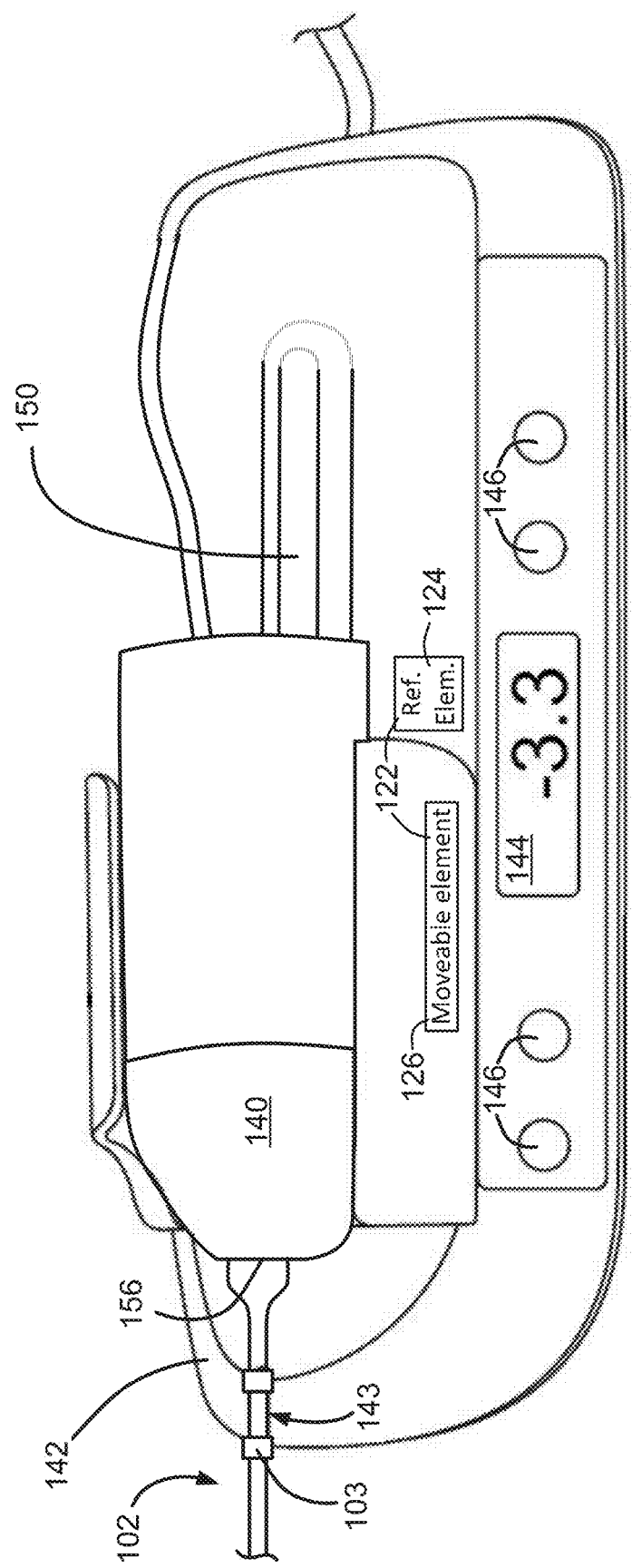
FIGS. 4A and 4B are perspective views of an illustrative translation mechanism of some intravascular imaging systems.

FIG. 4A shows an interface element 140 engaging a catheter 102 and secured to translation element 142. In some embodiments, the interface element 140 can be configured to translate relative to the translation element 142. During operation, the interface element 140 can be secured to the catheter 102 at an attachment point 156 and translated with respect to the translation element 142, for example via a track 150. The translation element 142 can be held stationary relative to the patient so that as the interface element 140 is translated relative to the translation element 142, the interface element 140 engages a portion of the catheter 102 and translates the transducer 108 through the patient's vasculature. In some embodiments, the translation element 142 defines the translation of the interface element 140 relative thereto. Translation can be effected, for example, by controls 146.

Figure 4B:
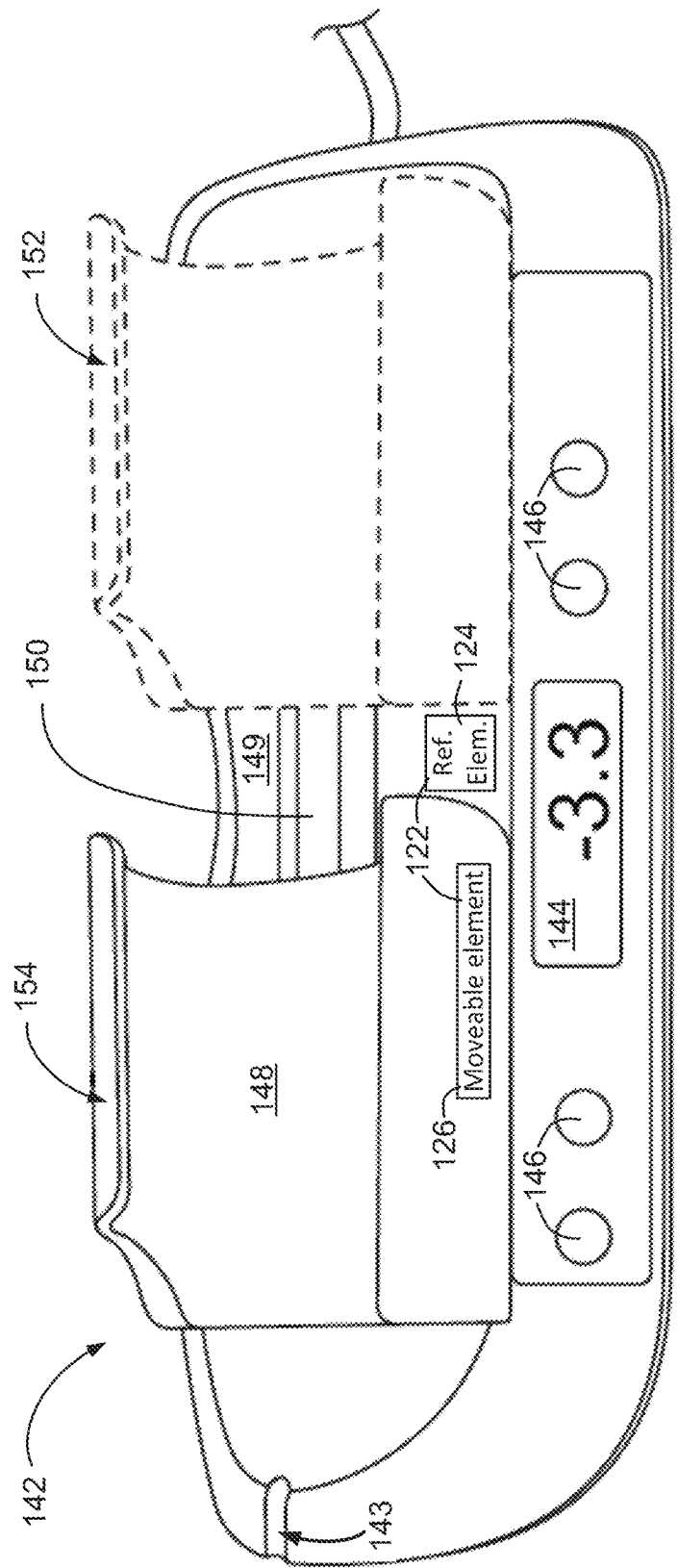

FIG. 4B shows an illustrative translation element 142. The translation element 142 can include a display 144 and controls 146 for user observation and manipulation of settings and actions of the translation mechanism and/or the intravascular imaging system. In some embodiments, the controls 146 allow for a user to control operation of the intravascular imaging system. For example, among various embodiments, a user can perform imaging functions, translate the transducer 108 and/or the catheter 102, rotate the transducer 108 or perform any other user function that can be initiated by a user via the controls 146.

Referring to FIGS. 4A-4B, the display 144 can display information pertaining to the intravascular imaging system. The display 144 can display information such as the relative positions of the catheter 102 and/or transducer, the relative positions of the reference element and movable element of the position sensor, the velocity at which motion is occurring, or any other relevant system parameters. In some embodiments, the display 144 can present a graphical user interface (GUI) to assist a user in operating the system via controls 146. Thus, among various embodiments, a user can cause a motor to translate the transducer within a patient's vasculature using, for example, a user interface on the intravascular imaging engine or the controls 146 and display 144 on the translation mechanism. As described, in some embodiments, a user can translate the transducer manually through a patient's vasculature without the use of a motor.

The translation element 142 can include a cradle 148 that may be configured to mate with the interface element 140 and a base 149 translationally coupled to the cradle 148. In some embodiments, the cradle 148 can translate relative to the base 149 along a track 150. In some such embodiments, when a catheter 102 is coupled to the interface element 140, and the interface element 140 is mated with the cradle 148, the translation element 142 can translate a transducer carried by the catheter 102 in a desired manner by translating the cradle 148 along the track 150. The cradle 148 of FIG. 4B is shown in two possible positions—a distal position 154, shown in solid lines, and a proximal position 152, shown in phantom. In many embodiments, the translation element 142 can translate the cradle 148 from the distal position 154 to the proximal position 152 in a pullback operation. It should be appreciated that in some intravascular imaging operations, the translation element 142 can be configured to translate between the distal position 154 and the proximal position 152 in either direction and/or to stop anywhere in between along the track 150.

According to some embodiments, the cradle 148 and base 149 of the translation element 142 as well as the interface element 140 can act to support the reference element 124 and the movable element 126 of the position sensor 122. For example, in some embodiments such as those shown in FIGS. 4A and 4B, the reference element 124 can be secured to a spot on the base 149 of the translation element 142 while the movable element 126 can be secured to the cradle 148 of the translation element 142. In such an embodiment, the position sensor 122 can determine relative position and movement between the cradle 148 and the base 149. The interface element 140 can be secured to the catheter 102 and the cradle 148 such that translating the cradle 148 along the track 150 causes the transducer to translate within the patient. If the base 149 is stationary relative to the patient, the relative motion between the cradle 148 and the base 149 corresponds to the relative motion of the transducer within the patient. In some embodiments, the movable element 126 can alternatively be secured to the interface element 140. Similarly, the relative movement between the interface element 140 and the base 149 can correspond to the relative motion of the transducer within the patient. It will be appreciated that securing the movable element 126 to the base 149 and the reference element 124 to the cradle 148 or interface element 140 results in the same relative motion between the movable element 126 and reference element 124 as the previously described embodiment, and can be used similarly.

In some embodiments, for example, the reference element 124 can be positioned anywhere along the base 149, including in or around the track 150. Likewise, movable element 126 can be positioned anywhere along the cradle 148, including an attachment feature for securing the cradle 148 to the base 149 along track 150. In some embodiments, the reference 124 and movable 126 elements are positioned such that they are closest together when the cradle 148 is in the furthest proximal position along the track 150. Alternatively, in some embodiments, reference 124 and movable 126 elements are closest together when the cradle 148 is in the distal most position along the track 150. As explained, the movable element 126 can similarly be positioned on the interface element 140 and operate similarly. In some examples, the movable element 126 is positioned on the bottom side of the interface element 140 so as to be as close to the base 149, and therefore the reference element 124 that it supports, as possible.

In some cases, the translation element 142 includes a groove 143 into which an anchor portion 103 of the catheter 102 can be secured. In some such embodiments, translation of the interface element 140 causes the transducer within the catheter 102 to translate within the catheter sheath, while anchor portion 103 causes the rest of the catheter to remain fixed. Accordingly, for example, the reference element 124 can be positioned on or near the groove 143 in the base 149 of the translation element 142 or the anchor portion 103 of the catheter 102, while the movable element 126 can be positioned on any portion of the translation element 142 that translates relative to such components, such as the cradle 148, the interface element 140 or a translating portion of the catheter 102 itself. In some embodiments, for example, movable element 126 can be disposed at or near the attachment point 156 between the catheter 102 and the interface element 140. It will be appreciated that various such combinations of positions for the reference element 124 and the movable element 126 of the position sensor 122 are possible and within the scope of the invention.

In some embodiments, the catheter 102 can comprise first and second telescoping portions, configured to telescope relative to one another in order to facilitate motion of the transducer 108. Telescoping portions can be used, for example, in conjunction with the anchor portion (103 in FIGS. 4A-4B) of the catheter 102 and the groove (143 in FIGS. 4A-4B) in the translation element (142 in FIGS. 4A-4B) to facilitate movement of a part of the catheter 102 and the transducer 108 with respect to a stationary part of the catheter 102 (e.g., the anchor 103 of FIGS. 4A-4B). FIGS. 5A and 5B are illustrative configurations of first and second telescoping portions 164, 166 as part of an intravascular imaging catheter 102 that can be used in intravascular imaging system. FIG. 5A shows a first telescoping portion 164 and a second telescoping portion 166 as part of an intravascular imaging catheter 102. It will be appreciated that, while illustrated as part of catheter 102 in the illustrated embodiments, telescoping portion can be external to the catheter in some systems. In the example shown in FIG. 5A, the first telescoping portion 164 recessed into an opening within the second telescoping portion 166. The first and second telescoping portions 164, 166 can be slidably coupled to allow relative movement therebetween.

FIG. 5B shows the first and second telescoping portions 164, 166 of the intravascular imaging catheter 102 of FIG. 5A, with the first telescoping portion 164 extending from the second telescoping portion 166. In many embodiments, the first and second telescoping portions 164, 166 can be configured to transition freely between the configurations shown in FIGS. 5A and 5B. That is, the first and second telescoping portions 164, 166 can "telescope" relative to one another. In some embodiments, one of the first and second telescoping portions 164, 166 can be fixed to a component of the intravascular imaging system that remains stationary relative to the patient, for example the translation element 142 of the translation mechanism 110 shown in FIGS. 4A-4B.

In some embodiments, the transducer 108 can be coupled to one of the first and second telescoping portions 164, 166 and not the other. In such arrangements, the telescoping portion not coupled to the transducer 108 can remain fixed while the other telescoping portion moves relative thereto, thereby causing motion of the transducer 108 relative to the stationary telescoping portion. Thus, the telescoping motion of the first and second telescoping portions 164, 166 can facilitate motion of the transducer 108. In an illustrative embodiment, the transducer 108 is coupled to the first telescoping portion 164 while the second telescoping portion 166 is fixed to a stationary component of the system 100. As motion of the transducer 108 is actuated (manual translation, motorized translation, etc.), the first telescoping portion 164 can translate within the second telescoping portion 166. In some embodiments, the transducer 108 can be coupled to the second telescoping portion 166 while the first telescoping portion 164 is fixed to a stationary component of the system 100. As motion of the transducer 108 is actuated (manual translation, motorized translation, etc.), the second telescoping portion 166 can translate on the outside of the first telescoping portion 164. In various configurations, the transducer 108 can be coupled to the first 164 or second 166 telescoping portion via a drive cable. Alternatively, in some systems, the first 164 or second 166 telescoping portion can be a part of the drive cable itself.

In some embodiments, the relative movement of the first and second telescoping portions 164, 166 of the catheter 102 can be correlated to the motion of the transducer 108 within a patient's vasculature. Accordingly, each of the movable element 126 and the reference element 124 of the position sensor 122 can be coupled to one of the first and second telescoping portions 164, 166. In the embodiment of FIGS. 5A-5B, the movable element 126 can be coupled to the first telescoping portion 164 while the reference element 124 can be coupled to the second telescoping portion 166. In this configuration, if the first telescoping portion 164 is coupled to the transducer 108 and the second telescoping portion 166 is fixed stationary relative to the patient, the relative motion between the movable element 126 and reference element 124 of the position sensor 122 correspond to the relative movement of the first and second telescoping portions 164, 166 relative to each other, and ultimately the relative movement of the transducer 108 within the patient. In some embodiments, the movable element 126 can be coupled to the second telescoping portion 166 while the reference element 124 can be coupled to the first telescoping portion 164. In this configuration, if the second telescoping portion 166 is coupled to the transducer 108 and the first telescoping portion 164 is fixed stationary relative to the patient, the relative motion between the movable element 126 and reference element 124 of the position sensor 122 corresponds to the relative movement of the first and second telescoping portions 164, 166 and the transducer 108 within the patient.

In addition to being disposed on a translation mechanism or catheter telescoping portions, components of the position sensor can be located in any number of suitable locations in an intravascular imaging system. In some embodiments, if one of the movable element and the reference element is coupled to the transducer in some way so that its position is correlated to the transducer position (e.g., via interface element of the translation mechanism or the first telescoping portion), while the other of the movable element and reference element is fixed relative to the patient (e.g., via a translation element of a translation mechanism or a telescoping portion), relative motion between the position sensor's movable element and reference element can correspond to relative motion of the transducer within the patient. According to some configurations, the movable element can be located on or near the transducer and/or drive cable while the reference element can be disposed on the catheter sheath through which the transducer and drive cable translate.

In some embodiments, one or both of the movable element or reference element of the position sensor can be disposed in a reference medical component. Referring to FIG. 1, in some embodiments, the reference medical component can comprise a surgical mat 119. In some configurations, the reference element can be disposed in a reference medical component remaining substantially stationary relative to the patient, while the movable element can be coupled to any component of the intravascular imaging system 100 with a position corresponding to that of the transducer 108. For example, the reference element can be disposed in a surgical mat 119 underneath the patient 118 while the movable element can be coupled to any of the relevant telescoping portion, an interface element of a translation mechanism 110, the catheter drive cable, or the transducer 108. In any such configuration, the relative motion between the reference element and the movable element of the position sensor can correspond to the relative motion between the transducer 108 and the patient 118.

Several system configurations regarding the position sensor have been described. Various combinations of the described configurations are also contemplated. For example, in some embodiments, the movable element of the position sensor can be coupled to a telescoping portion, which can in turn be coupled to the transducer 108, while the reference element is coupled to any of several components held stationary relative to the patient 118, such as a surgical mat 119, a complementary telescoping portion, the base of the translation mechanism, or any other such object. In general, movable element can be coupled to any component that generally translates with the transducer 108, while the reference element can be coupled to any component that remains stationary relative to the patient 118. In several such exemplary embodiments, the relative position of the movable element and the reference element ultimately correspond to the relative position of the transducer 108 in a patient's vasculature. Intravascular imaging systems according to some embodiments can comprise an intravascular imaging engine 112 configured to receive position information from the position sensor, as well as image information from the catheter. The intravascular imaging engine 112 can generate a display based on the image information and the position information.

Intravascular imaging systems such as those described can be used to generate one or more displays based on image and position information. FIG. 6 is a step-flow diagram outlining a method in which one or more displays can be generated. After the catheter is inserted into a patient by a system operator, an intravascular imaging engine such as those described herein can receive a command to perform an intravascular imaging function (200). The command can include parameters and scheduling of the imaging function. A user may command the intravascular imaging engine to perform the imaging function. The user can manually program the desired parameters for the imaging function.

The intravascular imaging engine can initiate the imaging function commanded in the intravascular imaging catheter (202). This can include interfacing with the catheter, sending control signals and/or power to the catheter, rotating the catheter and/or the transducer within the catheter, or any other initiation process for performing the imaging function. In some embodiments, any single or combination of initiation processes can be initiated manually via a user interface.

After initiating the imaging function (202), the intravascular imaging engine can receive image information from the catheter based on the performed imaging function (204). The image information can be in the form of electrical or other signals from the catheter and/or transducer. The intravascular imaging engine can additionally receive position information from a position sensor (206). As described, the position information can comprise information regarding the relative position of a reference element and a movable element, which can correspond to the relative position of the transducer within the patient.

After receiving image information and position information, the intravascular imaging engine can generate a display based on the received information (208). The display can be presented on a display where it can be viewed by a system user. The generated display can include, for example, a longitudinal image and/or a cross-sectional image corresponding to a single transducer location within a patient. In some systems, the generated display can be generated by the intravascular imaging engine in real-time and shown on the display as a live image. In some embodiments, the generated display can comprise a single snapshot of a cross section of a patient's vasculature triggered by a user, in which image and position information are captured for a single transducer location at a single time. In some embodiments, various generated displays are possible. In some systems, a user can select which mode of display is used (e.g., real-time, snapshot, etc.).

The intravascular imaging engine, based on received commands (e.g., step (200)) and memory, can determine if more information is to be acquired (210). In some embodiments, the user can decide whether more information will be acquired. If so, the intravascular imaging engine can initiate translation of the transducer within the patient (212). For example, in some systems, a selected mode of display, such as real-time display or a snap-shot display, selected by a user can be used to determine if more information is to be acquired (210). In some embodiments, the intravascular imaging system comprises a translation mechanism. The translation mechanism can be configured for automated translation via a motor and/or manual operation. In some such embodiments, the imaging engine can interface with the translation mechanism and initiate translation (212) directly via the motor. Some embodiments of the intravascular imaging system are configured for manual translation of the transducer. In such embodiments, the intravascular imaging engine can prompt the user to translate the transducer. After the transducer has been translated, an imaging function can again be initiated (202) and the process repeated. Once it is determined that no additional information is to be acquired (210), the generated display, image, and/or position information can be saved in memory (214). In some embodiments, the user can manually save information to memory. If all operations utilizing the catheter are complete, in various embodiments the catheter can be withdrawn from the patient either manually or automatically (214).

Receiving image information (204) and receiving position information (206) can involve receiving any number of sets of image and position information from any number of distinct positions of the movable element of the position sensor. In some embodiments, receiving image information (204) and receiving position information (206) can include receiving a first set of image and position information corresponding to a first position of the movable element of the position sensor and a second set of image and position information corresponding to a second position of the movable element of the position sensor, such that the first and second positions are distinct from one another.

Because, in some embodiments, the position of the movable element of the position sensor is correlated to the position of the transducer in the patient's vasculature, the received sets of image and position information can correspond to distinct locations of the transducer. In some embodiments, at any one of the movable element positions for which the image and position information are received, the image and position information can be associated with one another as having been received at a common transducer position. Each set of image information can correspond to image information generated from a unique location within the patient's vasculature. The sets of position information can provide details on the spatial relationships between the unique locations. This can allow for the combination of image and position information from multiple movable element positions and the construction of a combined image.

In some embodiments, image and position information are received from a series of transducer positions by way of performing a pullback operation (e.g., all the way across a region of interest in a patient's blood vessel). Pullback can comprise inserting a catheter into a patient's vasculature and performing an imaging function while retracting the transducer through the patient, thereby acquiring image and position information corresponding to a plurality of transducer positions. Pullback can be executed by a motor, and can be initiated by a user via the user interface of the intravascular imaging engine. A predetermined pullback operation can be performed, wherein the motor pulls the transducer back in a predetermined manner. In some embodiments, a user can manually control the operation of the motor and control the pullback operation. Motor controlled pullback can be automatically performed as part of an imaging schedule stored in memory. Automated pullback can include a feedback element configured to provide position information from the position sensor to the intravascular imaging engine, and the intravascular imaging engine can control the motor based on the position information. In some configurations, pullback can be performed entirely manually, in which a user manually translates the transducer within the patient while performing an imaging function. The execution of a pullback imaging operation can result in a plurality of sets of position and corresponding image information in which the relative spatial relationship between the sets of position information is known.

Image and position information from multiple movable element locations (i.e., transducer locations) can be combined to produce a three-dimensional volume of image information. When the relative transducer locations for each set of position and image information received are known, each set of image information can be arranged in a correct sequence and with appropriate spatial separation. In some embodiments, a single set of image data received by the intravascular imagine engine comprises a cross-sectional image of the patient's vasculature proximate the transducer. A single set of position information can include a relative longitudinal location of the transducer within the patient's vasculature. A second set of image and position information received from a second position can comprise a second cross-sectional image, and the relative longitudinal location of the transducer when the image was taken. The relative relationship between the first and second transducer location can be determined by the first and second set of position information. Accordingly, the first and second set of image information can represent cross-sectional images taken at longitudinal locations a known distance apart. The cross sections can be combined along a longitudinal axis and appropriately spaced to form a three-dimensional representation of the two sets of information.

In general, any number of sets of image and position information (i.e., unique cross-sections) can be combined in this way to build up a three dimensional representation of the surroundings of the transducer, such as a patient's vasculature. Such a representation can be referred to as a longitudinal image. FIG. 7 shows an exemplary longitudinal image as can be constructed by an embodiment of an intravascular imaging system. FIG. 7 shows a display 220 such as might be shown on the display 114 of FIG. 1, for example. Referring again to FIG. 7, display 220 can include a cross-sectional image 224 configured to display a set of image information 222 corresponding to a particular transducer location. The display 220 can include a longitudinal image 226 configured to show a longitudinally arranges series of sets of image information, each from a particular transducer 108 location and arranged according to the associated position information. A longitudinal image 226 can be such that the longitudinal axis represents the direction of translation of the transducer in a patient's body. Accordingly, each data point along horizontal axis of a longitudinal image 226 can have associated therewith a corresponding cross-sectional image 225. While FIG. 7 shows the axis representing transducer motion being the horizontal axis, it will be appreciated that such characteristics could alternatively describe a vertical axis, or any other orientation, and in some embodiments can generally be a longitudinal axis. In some embodiments, the longitudinal image 226 is essentially a side-view of a plurality of cross-sectional images stacked on one another and arranged according to their relative positions. In some embodiments, each of the cross-sectional images can include a small amount of longitudinal information, which can be used to fill in gaps between transducer positions from which image information was received.

The display 220 as shown in FIG. 7 can include image data 228. Image data 228 can include various pieces of information about the cross-sectional image 224, the longitudinal 226 image 226, the patient being imaged, other system information, etc. In some examples, image data 228 can include the patient name, a patient ID number, the time and date, frame number, and/or image information acquisition parameters such as an imaging frequency. In various embodiments, image data 228 can be displayed collectively in a single location on the display 220, or can be displayed across various locations. In the example of FIG. 7, image data 228 is located in multiple locations. In some embodiments, the display 220 can include a real-time display while continually performing one or more imaging functions. The display 220 can include a user interface 230 to provide command and control functionality to the user.

In some embodiments, the display 220 shown in FIG. 7 is part of the intravascular imaging engine. The display 220 can comprise a touch screen for user input and manipulation. In some embodiments, the user can perform various functions with regard to the generated display 220. In some examples, the user can manipulate the brightness and/or contrast of the display 220, save a screenshot to memory, initiate an imaging function such as a pullback operation, terminate an imaging function, and so on. In the case of a longitudinal image 226, in some embodiments, a user can select a point along the longitudinal axis in the longitudinal image 226 for which to display the associated cross-sectional image 224 of the corresponding transducer position.

Referring again to FIG. 1, methods of using an intravascular imaging system 100 include inserting the distal end 106 of a catheter 102, including a transducer 108, into the vasculature of a patient 118. A user 116 can initiate an imaging operation via a user interface 120 of an intravascular imaging engine 112 in which the transducer 108 provides image information to the intravascular imaging engine 112. The system 100 can include a position sensor including a reference element and a movable element, and configured such that the reference element is fixed relative to the patient and the movable element position is correlated to the position of the transducer 108. Accordingly, intravascular imaging engine 112 can receive position information from the position sensor. The intravascular imaging engine 112 can generate a display based on the received position and image information.

The user 116 can initiate translation of the transducer 108 within the patient 118, resulting in the intravascular imaging engine 112 receiving image and position information relating to a plurality of positions of the movable element 126, and therefore of the transducer 108. The intravascular imaging engine 112 can receive and combine this information into an aggregate image, such as a longitudinal image 226 of FIG. 7. Referring again to FIG. 1, the user 116 can manipulate or save the display via the intravascular imaging engine 112. In some embodiments, the user can select a portion of the longitudinal image from which to display a corresponding cross-sectional image.

Various aspects of the invention can be embodied in a non-transitory computer-readable medium. A non-transitory computer-readable medium can comprise executable instructions for causing a processor to receive image information from a transducer 108 located near the distal end 106 of an intravascular imaging catheter 102, and position information from a position sensor. The position sensor can comprise a movable element and a reference element and the position information can comprise a movable element position, representing the position of the movable element relative to the reference element and correlated to the transducer position. The non-transitory computer-readable medium can further contain executable instructions to cause the processor to generate a display based on the received image and position information. In some embodiments, the non-transitory computer-readable medium can be embodied in the intravascular imaging engine 112. In some embodiments, a non-transitory computer-readable medium can comprise executable instructions for causing a processor to perform any method discussed herein.

It should be appreciated that components described with regard to particular embodiments of the invention may be combined to form additional embodiments. Instructions embedded or encoded in a computer-readable storage medium may cause a programmable processor, or other processor, to follow the instructions prescribed. Computer readable storage media may include random access memory (RAM), read only memory (ROM), a hard disk, optical media, or other computer readable media.

Various examples have been described. These and other examples are within the scope of the following claims.

The invention claimed is:

1. An intravascular system comprising:
    an intravascular imaging catheter including a drive cable having a proximal end and a distal end, a transducer located in a transducer position near the distal end of the drive cable, a sheath through which the drive cable extends, and an anchor portion;
    a translation mechanism including an interface element configured to engage the drive cable of the intravascular imaging catheter and a translation element configured to engage and translate the interface element, the translation element of the translation mechanism including a groove configured to engage the anchor portion of the catheter to secure the anchor portion and the sheath of the catheter to the translation element such that translation of the interface element relative to the translation element causes the drive cable and transducer to move through the sheath;
    a position sensor including a movable element and a reference element, the movable element having a movable element position that is correlated to the transducer position and the reference element being positioned in a base of the translation element or on the anchor portion of the intravascular imaging catheter, the position sensor being configured to measure the movable element position relative to a position of the reference element; and
    an intravascular imaging engine coupled to the intravascular imaging catheter, the intravascular imaging engine being configured to receive image information from the intravascular imaging catheter and position information from the position sensor and to generate a display based on the image information and the position information.

2. The intravascular system of claim 1, wherein the movable element of the position sensor is positioned on the interface element of the translation mechanism.

3. The intravascular system of claim 1, wherein the movable element of the position sensor is positioned on the catheter.

4. The intravascular system of claim 1, wherein the image information and the position information comprise:
    a first set of image information and position information corresponding to a first movable element position, and
    a second set of image information and position information corresponding to a second movable element position that differs from the first movable element position.

5. The intravascular system of claim 1, wherein the interface element comprises a rotation mechanism configured to interface with the drive cable of the catheter and to rotate the transducer.

6. The intravascular system of claim 1, wherein the translation mechanism is motorized for automatic translation.

7. The intravascular system of claim 6, wherein the intravascular imaging engine is configured to instruct the translation mechanism to translate the transducer a predetermined amount based on feedback position information received from the position sensor.

8. The intravascular system of claim 1, wherein the translation mechanism includes a damping mechanism configured to facilitate smooth translation of the intravascular imaging catheter's transducer.

9. The intravascular system of claim 1, wherein the position sensor comprises at least one of a potentiometer or an encoder.

10. The intravascular system of claim 1, wherein the intravascular imaging engine includes a user interface configured to present the generated display to a user and to receive an input from the user, the generated display including a cross-sectional IVUS image comprising image information corresponding to one longitudinal location, and a longitudinal IVUS image comprising image data from a plurality of longitudinal locations, and wherein the input comprises a selection of a longitudinal location from the longitudinal IVUS image, and the displayed cross-sectional IVUS image corresponds to the selected longitudinal location.

11. A method for operating an intravascular imaging system that includes
   (i) a catheter having a drive cable including a proximal end and a distal end, a transducer located in a transducer position near the distal end of the drive cable, a sheath through which the drive cable extends, and an anchor portion,
   (ii) a position sensor including a movable element and a reference element, and
   (iii) a motorized translation mechanism including a motor capable of receiving commands for translating the transducer of the catheter within the sheath and a groove for interfacing with the anchor portion of the catheter to hold the sheath in place while the drive cable is moved therethrough, the reference element of the position sensor being located at or near the groove in the motorized translation mechanism, the method comprising:
   receiving a command to move the transducer a predetermined amount;
   while the anchor portion of the catheter is secured to the groove in the translation mechanism, translating the transducer through the sheath by the predetermined amount via the motorized translation mechanism while receiving position information from the position sensor, the position information being used as a feedback signal for automatically controlling the translation distance of the transducer through the sheath and comprising a movable element position relative to the position of the reference element in a base of the translation mechanism or on the anchor portion of the intravascular imaging catheter, the movable element position being correlated to a position of the catheter's transducer;
   while moving the transducer through the sheath, receiving image information from the catheter at a plurality of transducer positions based on an imaging function performed with the catheter in a patient's blood vessel, the received image information having corresponding position information based on position information received at or near the plurality of transducer positions; and
   generating a display based on the image information and the position information.

12. The method of claim 11, wherein the steps of receiving the image information and the position information comprise:
   receiving a first set of image information and position information corresponding to a first movable element position, and
   receiving a second set of image information and position information corresponding to a second movable element position that differs from the first movable element position.

13. The method of claim 11, wherein the imaging function comprises IVUS imaging.

14. The method of claim 13, wherein generating the display comprises generating a longitudinal image of the patient's blood vessel.

15. The method of claim 14, wherein the generated display comprises a longitudinal image and a cross-sectional image, and wherein generating the display further comprises receiving, via a user interface, a selection of a location in the longitudinal image and displaying a cross-sectional image corresponding to the selected location.

16. The method of claim 11, wherein the translation mechanism includes a damping mechanism configured to facilitate smooth translation of the transducer.

17. The method of claim 11, wherein receiving position information comprises receiving information from a potentiometer.

18. The method of claim 11, wherein receiving position information comprises receiving information from an encoder.

19. An intravascular imaging system, comprising:
   an intravascular imaging catheter comprising a drive cable having a distal end and a proximal end, a transducer located at or near the distal end of the drive cable, a sheath through with the drive cable extends, and an anchor portion;
   an interface element configured to engage the drive cable of the intravascular imaging catheter;
   a translation element configured to facilitate translation of the interface element;
   a position sensor including a movable element and a reference element, the movable element having a movable element position that is correlated to the transducer position, the position sensor being configured to measure the movable element position relative to a position of the reference element; wherein
   the translation element includes a groove configured to engage the anchor portion of the intravascular imaging catheter such that when the anchor portion of the catheter is engaged with the groove and the interface element engages the drive cable of the intravascular imaging catheter, motion of the interface element relative to the groove of the translation element causes the drive cable to move through the sheath;
   the reference element of the position sensor is positioned in a base of the translation element or on the anchor portion of the intravascular imaging catheter;
   the movable element of the position sensor is positioned on an element that translates relative to the groove as the interface element moves via the translation element; and an intravascular imaging engine coupled to the intravascular imaging catheter, the intravascular imaging engine being configured to receive image information from the intravascular imaging catheter and position information from the position sensor, and to generate a display based on the image information and the position information.

20. The intravascular system of claim 19, wherein the translation element comprises a base and a cradle that is translationally coupled to the base and is configured to mate with the interface element.

21. The intravascular system of claim 20, wherein the groove of the translation element is positioned on the base of the translation element.

22. The intravascular system of claim 19, wherein the translation element comprises a motor configured to move the interface element relative to the groove in the translation element such that the drive cable moves within the sheath.

* * * * *